United States Patent

Obayashi et al.

[11] Patent Number: 4,724,209
[45] Date of Patent: Feb. 9, 1988

[54] PROCESS FOR PRODUCING RESTRICTION ENZYME

[75] Inventors: Akira Obayashi, Uji; Nobutsugu Hiraoka, Mukoo; Keiko Kita, Kyoto; Hiroshi Nakajima, Ootsu, all of Japan

[73] Assignee: Takara Shuzo Co., Ltd., Kyoto, Japan

[21] Appl. No.: 783,634

[22] Filed: Oct. 3, 1985

[30] Foreign Application Priority Data

Nov. 9, 1984 [JP] Japan .................... 59-237242

[51] Int. Cl.$^4$ ............... C12N 9/22; C12N 15/00; C12Q 1/68; C12R 1/01
[52] U.S. Cl. ................... 435/199; 435/172.1; 435/6; 435/822; 935/77
[58] Field of Search ............... 435/199; 935/77

[56] References Cited

PUBLICATIONS

Roberts, Nucleic Acid Research, vol. 11, No. 1, pp. r135–r167, (1983).

Primary Examiner—Lionel M. Shapiro
Attorney, Agent, or Firm—Wenderoth, Lind & Ponack

[57] ABSTRACT

A process for producing a restriction endonuclease capable of recognizing the nucleotide sequence

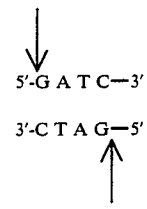

(wherein A, C, G and T represent adenosine, cytidine, guanosine and thymidine, respectively) on a DNA chain and specifically cleaving the double-stranded chain at the arrow-marked positions. This process comprises growing a microorganism belonging to the genus Halococcus and capable of producing said restriction endonuclease, and collecting the enzyme thus formed from the culture broth.

1 Claim, No Drawings

PROCESS FOR PRODUCING RESTRICTION ENZYME

This invention relates to a process for producing a restriction enzyme. More particularly, it relates to a process for producing a restriction enzyme formed by microorganisms belonging to the genus Halococcus.

Restriction enzymes are endonucleases that are capable of recognizing a specific sequence of bases on a deoxyribonucleic acid (DNA) molecule and of cleaving the doublestranded DNA chain at specific sites. As a result of recent progress in molecular genetics, biochemistry and related sciences, it is now clear that DNA is the carrier of genetic information, and restriction endonucleases have been extensively used for various purposes (clarification of genetic diseases, mass production of genetic materials based on genetic engineering, etc.). About 100 kinds of endonucleases have so far been isolated from many microorganisms, each being identified by the specific base sequence it recognizes and by the pattern of cleavage.

Of these, Mbo I produced by *Moraxella bovis* (ATCC 10900) [(Nucleic Acids Res., Vol. 11, r135 (1983)] is known as a restriction endonuclease which recognizes the base sequence as shown below and cleaves the DNA chain at the arrow-marked positions,

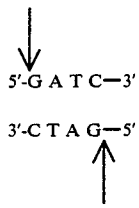

5'-G A T C—3'

3'-C T A G—5'

(wherein A, C, G and T represent adenosine, cytidine, guanosine and thymidine, respectively).

Mbo I, however, has problems for its industrial application. These include its low production yield from *Moraxella bovis*, and unavoidable contamination with Mbo II.

The object of this invention is to provide a process for industrial production of a restriction endonulease having the same recognition base sequence and cleavage sites as Mbo I.

Thus this invention relates to a process for producing a restriction endonuclease capable of recognizing the base sequence as shown below and specifically cleaving the DNA chain at the arrow-marked positions, which comprises growing a microorganism belonging to the genus Halococcus and capable of producing said enzyme, and collecting the enzyme thus formed from the culture broth,

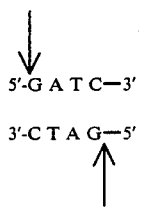

5'-G A T C—3'

3'-C T A G—5' wherein A, C, G and T represent adenosine, cytidine, guanosine and thymidine, respectively).

We have found that an enzyme having the same recognition base sequence and cleavage sites as Mbo I can be produced by microorganisms belonging to genus Halococcus, and that it can be easily isolated in a pure form because no other restriction enzyme is formed. This invention was accomplished based on these findings.

Any species of Halococcus that is capable of producing this enzyme may be used for the purpose of this invention. A typical example is *Halococcus acetoinfaciens* IAM 12094 stocked at the Institute of Applied Microbiology, University of Tokyo. This microorganism has also been deposited at Fermentation Research Institute Agency of Industrial Science and Technology, Japan under the accession number FERM BP-942.

For cultivation of these microorganisms, any culture medium may be used if it contains a proper combination of carbon sources, nitrogen sources, inorganic salts and other nutrients assimilable by the microorganism employed. The preferred pH of the medium is in the range from 4.5 to 8.0. Any of the shaking culture, agitation culture and aeration culture methods may be used, but culture with aeration and agitation is most peferable for mass production. Cultivation may be carried out at any temperature that allows formation of this enzyme, but the preferred range is from 30 to 37° C. Cultivating time varies with other conditions; cultivation should be continued until a maximum output of this enzyme is achieved.

This enzyme is accumulated principally inside bacterial cells, which can be separated from the culture broth, for example, by centrifugation.

This enzyme can be extracted and purified by using known techniques commonly employed for restriction endonucleases. The collected microbial cells are dispersed in a suitable buffer, and then broken down by ultrasonic treatment to allow extraction of the endonuclease by the buffer solution. After removal of the residue by ultracentrifugation, ammonium sulfate was added to the supernatant for salting out, and the precipitate which separated out was dissolved in a potassium phosphate buffer (pH: 7.5) and dialyzed against a buffer of the same composition. The dialyzate was purified by ion-exchange chromatography on phosphocellulose and DEAE-cellulose, and by affinity chromatography on heparin-Sepharose, giving the endonuclease of this invention.

The activity of this enzyme was determined by the method described below. A substrate solution of the composition shown in Table 1 was prepared.

TABLE 1

| | |
|---|---|
| 10 mM | Tris-HCl, pH: 7.5 |
| 7 mM | MgCl$_2$ |
| 175 mM | NaCl |
| 7 mM | 2-Mercaptoethanol |
| 0.01% | Bovine serum albumin |
| 1.0 μg | Dam$^-$λ-DNA |

This substrate solution (50 μL) was preheated to 37° C., the endonuclease of this invention to be tested was added to allow the enzymatic reaction to proceed at that temperature, and the reaction was stopped 60 minutes later by addition of a terminator solution (1% SDS, 50% glycerol, 0.02% Bromophenol Blue). The reaction mixture was applied to a 1% agarose slab gel, and electrophoresis was conducted at a constant voltage of 10 V/cm for one to two hours. The buffer solution used was 90 mM Tris-borate buffer ( pH: 8.3 ) containing 2.5 mM EDTA.

DNA bands can be detected by UV irradiation if 0.5 μg/ml ethidium bromide is previously added to the gel. Electrophoresis was regarded as complete when the number and intensity of the bands for DNA fragments no longer changed.

The enzyme activity which ensures complete decomposition of 1 μg Dam$^-\lambda$—DNA after one hour's reaction at 37° C. was defined as one unit.

The restriction enzyme of this invention has the physicochemical properties as described below.

(1) Action and substrate specificity

This endonuclease is capable of recognizing and cleaving the base sequence as shown below on a double-stranded DNA molecule, and is an isoschizomer of the known endonucleases Mbo I,

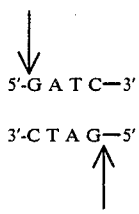

The recognition sequence of this enzyme was determined by using Dam$^+\lambda$—DNA ( product of Takara Shuzo Co., Ltd. ) and Dam$^-\lambda$—DNA as substrate. The enzyme of this invention cleaved Dam$^-\lambda$—DNA to form more than 50 fragments, but showed no action upon Dam$^+\lambda$—DNA. This suggested that this enzyme has, in its recognition site, the base sequence of which is recognized by Dam genes and undergoes methylation at A. To prove this, the known restriction endonuclease Mbo I was allowed to act upon Dam$^-\lambda$—DNA. The cleavage patterns thus obtained were identical to those with the restriction enzyme of this invention. Based on these findings, it was concluded that the nucleotide sequence the present endonuclease can recognize is 5'-GATC-3'.

The positions of cleavage by restricton endonuclease of this invention was determined by synthesizing an oligonucleotide carrying the recognition sequence of the enzyme of this invention, allowing the enzyme of this invention to act upon it, and measuring the chain lengths of resulting fragments. The experimental procedure is detailed below.

Oligonucleotide d ( GCAGATCTGC ), which is self-complementary in nature, was synthesized by the solid phase method, the 5'-terminals were labelled with polynucleotide kinase and [γ—$^{32}$P]ATP, and the resulting oligonucleotide molecules were annealed into a double-stranded DNA. This was cleaved by the enzyme of this invention, and the reaction products were analyzed on a DEAE-cellulose thin-layer plate ( Masherey and Nagel Co. ), giving labelled spots for trinucleotide, 5'-GCA.

Based on the results obtained above, it was concluded that the endonuclease of this invention recognizes the base sequence as shown below and cleaves the DNA at the arrow-marked positions,

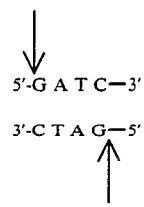

(2) Optimal conditions for enzymatic activity (a) Optimal temperature

The optimal temperature for this enzyme is about 45° C.

(b) Optimal pH

The optimal pH for this enzyme is in the range from 7.1 to 7.5.

(c) Salt concentration

The optimal enzymatic activity is exhibited at NaCl and KCl concentrations as high 175 to 300 mM.

The following Examples further illustrate this invention but are not intended to limit its scope.

EXAMPLE 1

A culture medium ( 500 ml .) of the composition shown in Table 2 below was charged in each of ten 2-liter conical flasks and sterilized in a usual way.

TABLE 2

| | |
|---|---|
| Bactotryptone | 10 g |
| Yeast extract | 5 g |
| Glucose | 1 g |
| NaCl | 30 g |
| Deionized water | 1 l |
| pH | 7.2 |

*Halococcus acetoinfaciens* IAM 12094 was propagated in a medium of the same composition as above at 35° C. for 27 hours by the shake culture method, 200 ml of the inoculum thus obtained was inoculated to the culture medium in the 2-liter conical flasks prepared above, and cultivation was continued at 35° C. for 13 hours under agitation. The grown cells were collected by a refrigerated centrifuge ( wet yield: about 15 grams from 5 liters of culture medium ).

The microbial cells ( 15 g ) were dispersed in 200 ml of an extractive buffer ( 20 mM Tris-HCl, pH: 7.5, 10 mM 2-mercaptoethanol ), the dispersion was subjected to ultrasonic treatment to break down the cell walls, and the resulting mixture was centrifuged for one hour ( at 100,000×g ) to remove the residue.

To the extract of enzyme thus obtained was added ammonium sulfate to 80% saturation, the precipitate which separated out was collected by centrifugation and dissolved in a buffer solution A ( 10 mM potassium phosphate buffer, pH: 7.5, 10 mM 2-mercaptoethanol, 5% glycerol ), and the solution was dialyzed overnight against buffer A.

The dialyzate was adsorbed on phosphocellulose ( product of Whatman Co., P-11 ), which was packed in a 20×80 mm column and equilibrated with buffer A, the column was washed with buffer A, and the adsorbed portion was eluted with buffer A containing KCl ( linear concentration gradient from 0 to 1.0 M ). Activity of the enzyme of this invention was detected in fractions of 0.05 to 0.18 M KCl concentration.

These active fractions were joined together, the combined solution was dialyzed overnight against buffer A, and the dialyzate was adsorbed, on DEAE-cellulose (Whatman, DE-52), which was packed in a 12×90 mm column and equilibrated with buffer A. After washing with buffer A, the adsorbed portion was eluted with buffer A containing KCl (linear concentration gradient from 0 to 1.0 M). Activity of the enzyme of this invention was detected in fractions of 0.06 to 0.14 M KCl concentration.

These active fractions were collected together, the combined solution was dialyzed overnight against buffer solution A, and the dialyzate was adsorbed on heparin-Sepharose (Pharmacia Fine Chemicals, CL-6B) packed in a 8×100 mm column and equilibrated with buffer A. After washing with buffer A, the adsorbed portion was eluted with buffer A containing KCl (linear concentration gradient from 0 to 1.5 M). Activity of the enzyme of this invention was detected in fractions of 0.25 to 0.35 M KCl concentration.

The active fractions were joined together, and the combined solution was dialyzed against a buffer containing 0.1 M KCl and 50% glycerol, giving a preparation of this enzyme.

This preparation contained no non-specific nuclease nor phosphatase.

Thus 3,000 units of this enzyme was obtained from 15 g of wet microbial cells.

As is apparent from the foregoing, this invention provides an advantageous method for producing an endonuclease having the same recognition sequence and cleavage positions as Mbo I on an industrial basis.

What we claim is:

1. A process for producing a restriction endonuclease capable of recognizing the nucleotide sequence as shown below on a DNA chain and specifically cleaving the double-stranded chain at the arrow-marked positions, which comprises growing the microorganism *Halococcus acetoinfaciens* FERM BP-942 capable of producing said restriction endonuclease, and collecting the enzyme thus formed from the culture broth,

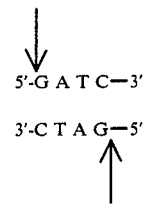

wherein A, C, G and T represent adenosine, cytidine, guanosine and thymidine, respectively.

* * * * *